United States Patent [19]
Tihon

[11] Patent Number: 5,626,578
[45] Date of Patent: May 6, 1997

[54] RF VALVULOTOME

[76] Inventor: Claude Tihon, 11304 Bluestem La., Eden Prairie, Minn. 55347

[21] Appl. No.: 437,020

[22] Filed: May 8, 1995

[51] Int. Cl.⁶ .................................................. A61B 17/39
[52] U.S. Cl. ................................................. 606/48; 606/50
[58] Field of Search .................................. 606/48, 50, 51

[56] References Cited

U.S. PATENT DOCUMENTS

| 4,791,913 | 12/1988 | Maloney . |
| 4,924,882 | 5/1990 | Donovan . |
| 4,952,215 | 8/1990 | Ouriel et al. . |
| 5,133,725 | 7/1992 | Quadri . |
| 5,171,316 | 12/1992 | Mehigan . |
| 5,234,450 | 8/1993 | Segalowitz . |
| 5,284,478 | 2/1994 | Nobles et al. . |

FOREIGN PATENT DOCUMENTS 0558039  9/1993  European Pat. Off. ............... 606/50

Primary Examiner—Lee S. Cohen
Attorney, Agent, or Firm—Haugen and Nikolai, P.A.

[57] ABSTRACT

A RF valvulotome and method of use is described. The valvulotome comprises an elongated, flexible polymeric tube or rod supporting a pair of paddle members at its distal end, the paddle members defining opposed facing surfaces having a gap therebetween. A pattern of metallization, comprising electrodes, are formed on the opposed facing surfaces and means are provided for applying RF energy between the electrodes after the instrument has been introduced into a vein and advanced to the point where the cusp of a vein valve is disposed in the gap. In a preferred embodiment, the paddles are movable toward and away from the center of the instrument and may incorporate a flushing lumen through which saline may be injected for effecting valve closure and facilitating placement of the paddle members within the pockets defining the valve. An optical-fiber bundle may also be passed through the lumen of the instrument to facilitate viewing of the internal vein structure as the catheter is being advanced.

25 Claims, 6 Drawing Sheets

5,626,578

RF VALVULOTOME

BACKGROUND OF THE INVENTION

I. Field of the Invention

This invention relates generally electrosurgical instruments, and more particularly to a bipolar electrosurgical instrument especially designed for carrying out a valvulotomy procedure on a vein to disable the venous valves.

II. Discussion of the Prior Art

Vein grafts are frequently used to replace segments of obstructed arteries for the continuation of blood flow in an arterial bypass procedure. In the case of an in situ bypass, where the vein is left essentially in place, an instrument called a valvulotome is used to render the valves in the vein inoperative. Arteries have smooth and unobstructed interior surfaces while peripheral veins have valves which insure a primary direction of blood flow back to the heart. In an in situ saphenous vein bypass, the saphenous vein, which normally returns the blood from the ankle upwardly through the leg, takes over the function of the occluded segments of femoral artery to carry blood from the leg to the ankle. In order for the segment of saphenous vein to carry on the function of the femoral artery, the series of one-way valves in the vein must be disabled.

To date, various valve stripping instruments have been devised for cutting or removing the valvular obstructions to the distal arterial flow. Instruments used for valvulotomy procedures have included single and double bullet-shape metal strippers employing incising parts of different shapes, such as described in the Ouriel et al. U.S. Pat. No. 4,952,215. Other valvulotomes have long, thin handles supporting curved, hook-like incising tips, such as is described in the Donovan U.S. Pat. No. 4,924,882. These instruments are designed to be introduced into the vein and displaced from the distal to proximal direction, and to incise the valves upon pulling the device backward so as to engage the valves cusps and cut through the valves. These mechanical valvulotomes must move forward and backward, with the cutting blades against the stationary valve cusps to cut the valves.

The use of razor sharp cutting blades inside the delicate vein poses the possibility of injury to the endothelium, as well as splitting and destruction of the vein, rendering it unsuitable as a graft. Further, the sharp mechanical devices of the prior art can accidentally engage the many side branches of the vein and cause unwanted cuts and tears. Though the precise cause for post-operative atherosclerosis is not known, endothelium injury has been discussed as a likely culprit.

When it is considered that the saphenous vein is larger toward the thigh and becomes noticeably smaller at the ankle, the current mechanical valvulotome devices are not able to accommodate the gradient in diameter of the vein. The gradation in size of the vein is addressed by repeatedly exchanging valvulotomes of different sizes at different regions of the vein. In addition to lengthening the time for the procedure, the frequent exchanging of the different sizes of valvulotomes involves additional axial movements of the device inside the vein, thus further increasing the possibility for injury to the endothelial layer. As mentioned above, in the standard procedure, using prior art valvulotomes as the different instruments are passed in moving in the proximal direction from the ankle towards the thigh, a need arises to make additional incisions along the length of the vein to allow valvulotomes of larger sizes to be inserted. This requires later suturing and creates a discontinuity in the vein which may later become the site of an atherosclerotic lesion.

In cardiac surgery, autologous reversed saphenous vein grafting has become routine for aorta-coronary bypass surgery. With this procedure, the valves within the vein are left intact, and the vein itself is reversed. The distal portion of the vein graft is usually larger in diameter than the replaced coronary artery, resulting in reduced blood flow velocity in the vein graft compared with that in the coronary artery. The patency rate of the coronary vein grafts goes from 85 percent at the end of the first year, post-operatively, to approximately 60 percent in five years. At 10 years, atherosclerosis becomes the major cause of coronary vein graft failure. Studies suggest that valves do not open fully during reverse blood flow and cause a decreased graft blood flow rate at the obstruction-related points. These intact, non-collapsed valve cusps may also cause sufficient turbulence to the laminar flow to become a situs for thrombus formation. Additional experience has shown that when more than one valve is present in the saphenous vein graft, occlusion, thrombus formation and accelerated progressive atherosclerosis seem to occur in correlation to the number of valves.

The function of a valvulotome is to disable vein valves such that a segment of vein can be used as a graft by bypass procedure without having to reverse its orientation relative to direction of blood flow.

Examples of typical prior art valvulotome devices are described in the Maloney U.S. Pat. No. 4,791,913; the Nobles U.S. Pat. No. 5,284,478; the Mehigan U.S. Pat. No. 5,171,316; the Ouriel et al. U.S. Pat. No. 4,952,215; the Quadri U.S. Pat. No. 5,133,725; and the Segalowitz U.S. Pat. No. 5,234,450.

From the foregoing discussion of the prior art, it is apparent that there is a need for an improved valvulotome which can be advanced in a retrograde direction relative to venous blood flow (proximal to distal) and operated to disable, by cutting, valve cusp material with a minimum of instrument exchanges and with minimal damage to the endothelium.

SUMMARY OF THE INVENTION

The foregoing need for an improved valvulotome is met by the present invention which comprises a bipolar electrosurgical instrument having an elongated, flexible catheter whose cross-sectional size permits its insertion into a vein to be treated. Disposed at the distal end of the catheter are first and second spaced-apart paddle members dimensioned to fit within opposing pockets of venous valves. The paddle members have opposed facing surfaces, each with a pattern of metallization thereon. A pair of conductors extend through a lumen of the catheter from the proximal end to the distal end and are individually electrically joined to the metallization patterns on the opposed surfaces of the paddle members. By advancing the paddle members into the pockets to straddle the cusps of the valves and then energizing a RF generator connected to the pair of conductors, the membranous cusp tissue disposed between the electrodes is ablated.

In accordance with a further embodiment of the invention, the paddle members disposed at the distal end of the elongated flexible catheter are made movable relative to one another so that the gap between the opposed facing surfaces can be opened and closed, thereby facilitating placement of the paddle members within the closed valves prior to the ablation step.

In that the paddle members can be smoothly rounded and need not have razor sharp edges to effect cutting, there is a lesser propensity toward damage of the endothelial lining of the veins as the instrument is advanced in the distal direction from one valve to the next. Equally important is the safety of the procedure in removing or retrieving the valvulotome instrument from the vein. The smoothly profiled instrument will again spare the vessel of injury.

By providing a fluid injection port on the handle of the instrument, which is in fluid communication with a lumen extending the length of the instrument, saline can be injected in the retrograde direction to facilitate the closing of the valves, resulting in an enlarged target for entry of the paddle members. It is also a feature of the invention that a fiber-optic viewing system can be employed, allowing the surgeon to view the working end of the instrument in relation to the valve structures to be ablated.

DESCRIPTION OF THE DRAWINGS

These and other features of the invention will become apparent to those skilled in the art from the following detailed description of a preferred embodiment, especially when considered in conjunction with the accompanying drawings in which like numerals in the several views refer to corresponding parts.

DESCRIPTION OF THE PREFERRED EMBODIMENT

Figure 1:
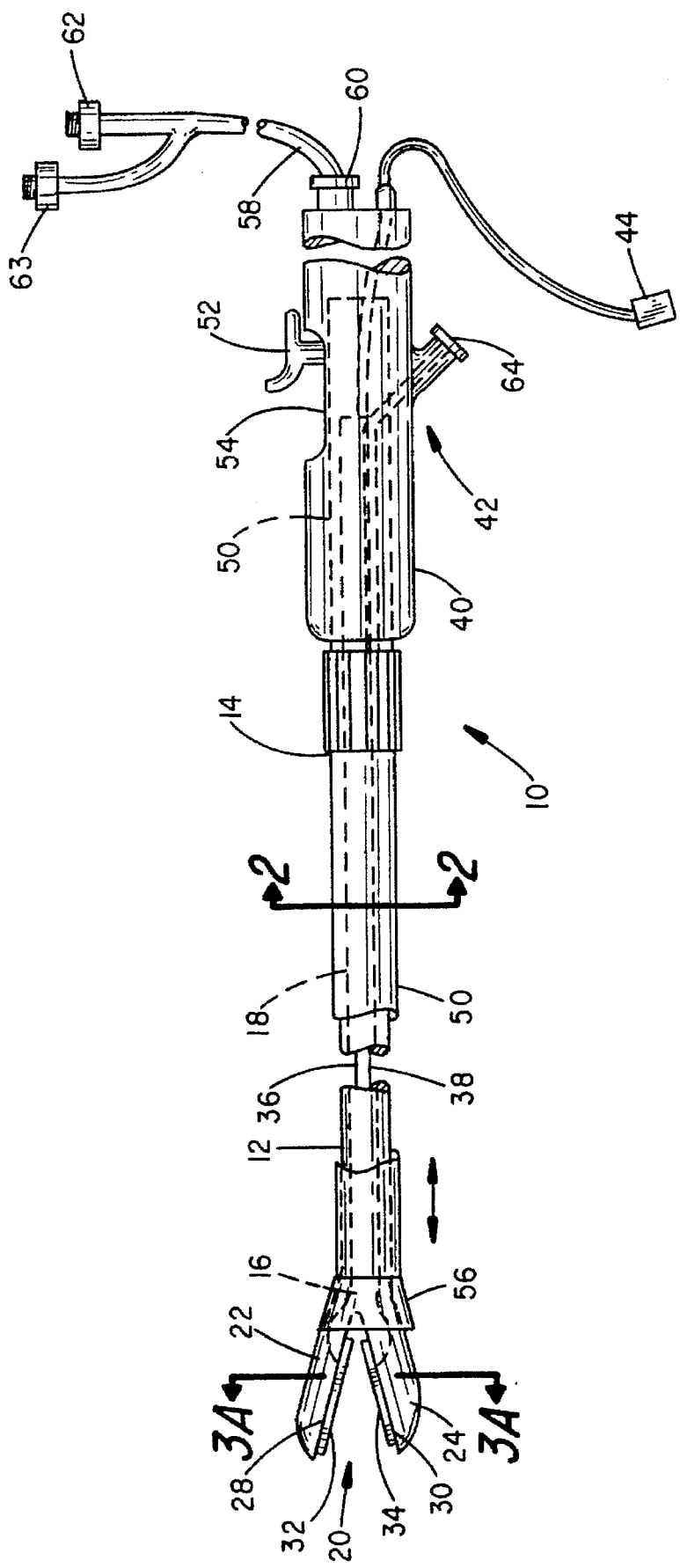
FIG. 1 is a side elevational view of a valvulotome instrument comprising a preferred embodiment of the present invention.
Figure 3:
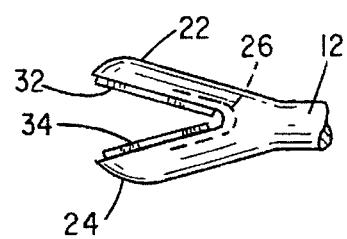
FIG. 3 is an enlarged partial view of the distal end of the instrument of FIG. 1.

Referring to FIG. 1, there is shown a side elevational view of the valvulotome instrument constructed in accordance with a first embodiment of the invention. The instrument is indicated generally by numeral 10 and is seen to include an elongated, flexible, plastic, tubular catheter 12 having a proximal end 14, a distal end 16 and at least one lumen 18 extending between the proximal and distal ends. Affixed to the distal end 16 of the elongated tubular catheter 12 is a jaw assembly 20 comprising a first paddle member 22 and a second paddle member 24 which are integrally joined together and to the tubular member 12. A suitable biasing means, such as a leaf spring 26 (FIG. 3) may be embedded into the material comprising the jaw assembly 20 to normally maintain the paddle members 22 and 24 open relative to one another as is illustrated in FIGS. 1 and 3. Those skilled in the art will appreciate that the inclusion of a leaf spring, as at 26, can be omitted where the memory property of the material employed in fabricating the jaw assembly 20 normally urges the jaw members 22 and 24 apart.

With continued reference to FIGS. 1 and 3, the paddle members 22 and 24 have opposed facing surfaces 28 and 30 and each of these major surfaces has a pattern of metallization 32 and 34 thereon. The metallization patterns 32 and 34 comprise bipolar electrodes. Conductors 36 and 38 connect to the electrodes and run through a lumen 18 of the tube 12 and out through the stationary portion 40 of a handle assembly 42 that is affixed to the proximal end 14 of the catheter 12. The wires 36 and 38 terminate in a connector 44 adapted to mate with a corresponding connector on an electrosurgical generator (not shown).

Figure 3A:
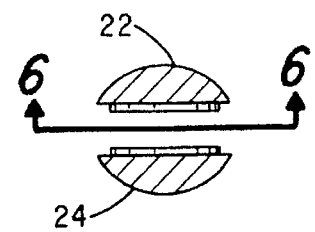
FIG. 3A is a cross-sectional view taken along the line 3A—3A in FIG. 1.
Figure 4:
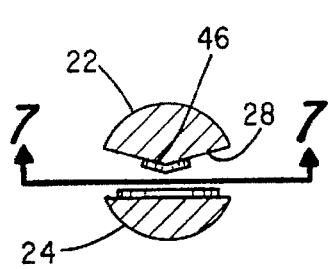
FIG. 4 is a cross-sectional view of the jaw portion of the instrument in FIG. 1 in accordance with an alternative electrode configuration.
Figure 6:
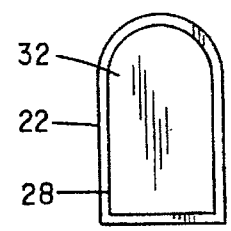
FIG. 6 is a view taken along the line 6—6 in FIG. 3A.
Figure 7:
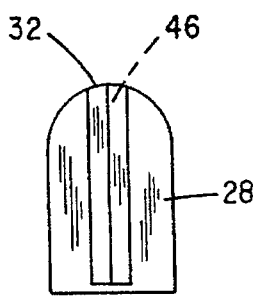
FIG. 7 is a view taken along the line 7—7 in FIG. 4.

FIG. 3A is a cross-sectional view taken along the line 3A—3A in FIG. 1. It shows that when the paddle members 22 and 24 are closed against one another, they form a generally bullet-shaped configuration. The individual paddle members can thus be referred to as being "hemi bullet" shaped. The pattern of metallization can be varied to suit a particular application. FIG. 6 shows the pattern 32 as a generally flat electrode covering substantially the entire facing surface 28 thereof. Alternatively, as illustrated in FIGS. 4 and 7, one or both of the facing surface 28 may be non-planar, and preferably comprise first and second flat surfaces intersecting at an obtuse angle to form an apex along a line 46. The metallization on the opposing face of paddle member 24 may be like that shown in FIG. 6 and, being of a greater surface area, will function as the indifferent or return electrode of the bipolar pair.

Figure 5:
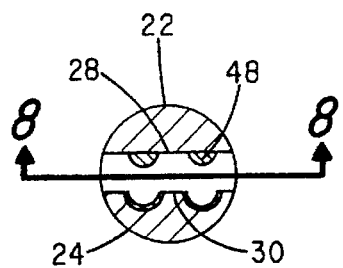
FIG. 5 is a cross-sectional view taken through the jaws of the instrument of FIG. 1 in accordance with still another electrode configuration.
Figure 8:
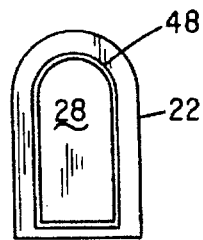
FIG. 8 is a view taken along the line 8—8 in FIG. 5.

With reference to FIGS. 5 and 8, there is shown another possible arrangement for the paddle members 22 and 24 of FIG. 1. Here again, the opposing facing surfaces 28 and 30 are non-planar with the surface 28 having a pattern of metallization in the form of a raised wire loop 48 (FIG. 8). The opposed facing surface 30 of the paddle member 24 has a groove formed therein and the surface of the groove is metallized and positioned to receive the raised loop electrode 48 when the jaws are made to close against one another.

Referring again to FIG. 1, coaxially surrounding the elongated flexible catheter 12 is a tubular sheath 50 which is secured at its distal end to a thumb slide member 52 of the handle assembly 42 so that as the thumb slide member 52 is moved back and forth in a longitudinal slot 54, the outer tubular sheath 50 is correspondingly displaced longitudinally about the catheter body 12 which it surrounds.

The outer tubular sheath 50 terminates at its distal end in a flared section 56 that cooperates with the rounded exterior surfaces of the paddle members 22 and 24 whereby displacement of the tubular sheath in the distal direction, via movement of the movable slide member 52 relative to the stationary member 40 of the handle assembly 42, forces the jaws 22 and 24 to close. Likewise, retraction of the outer tubular sheath 50 in the proximal direction allows the biasing spring 26 to reopen the jaws. With no limitation intended, the outside diameter of the flared section 56 may be in the range of from 2-5 mm (6 fr–15 fr) depending upon the size of the patient.

Figure 2:
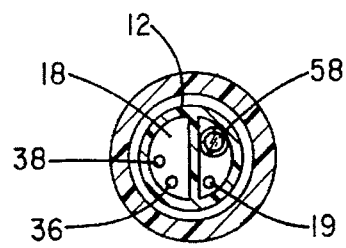
FIG. 2 is a cross-sectional view taken along the line 2—2 in FIG. 1.

With reference to FIG. 2, the inner catheter 12 may comprise a dual lumen tube with the insulated wires 36 and 38 extending through lumens 18 and 19 thereof. A fiber-optic bundle 58 may also extend through the second lumen 19. The fiber-optic bundle preferably comprises a plurality of viewing fibers encased in an outer sheath as well as one or more illumination fibers also enclosed by that sheath. The fiber-optic bundle 58 may be of the type described in the Utsumi et al. U.S. Pat. No. 4,867,529, and it has its object lens positioned so as to illuminate the scene proximate the paddle members 22 and 24 and to pick up an image of the illuminated tissue structures. The fiber-optic bundle 58 extends the length of the lumen 19 and then exits the handle assembly 42 via a Touhy-Borsch type fitting 60. The fiber-optic bundle then terminates at its proximal end in bifurcated connectors 62 and 63, allowing it to be connected to a suitable light source and to conventional viewing optics known in the art.

It is also contemplated that the lumen 19 of the catheter 12 may be connected to a source of saline through a port 64 in the handle, whereby the saline can be ejected out the distal end of the tubular catheter 12 during the course of a valvulotomy procedure to assist in closing a venous valve, thereby aiding in the placement of the jaw assembly 20 within the pockets defining the cusps of that valve in a manner yet to be described.

Figure 10:
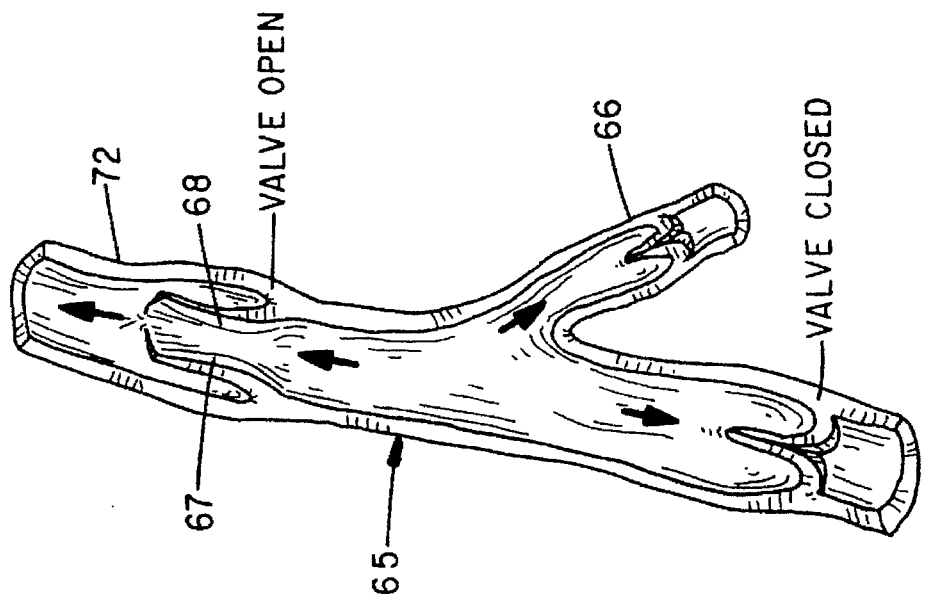
FIG. 10 is a longitudinal cross-sectional view taken through a segment of vein showing venous valves in both an open and a closed condition.
Figure 9:
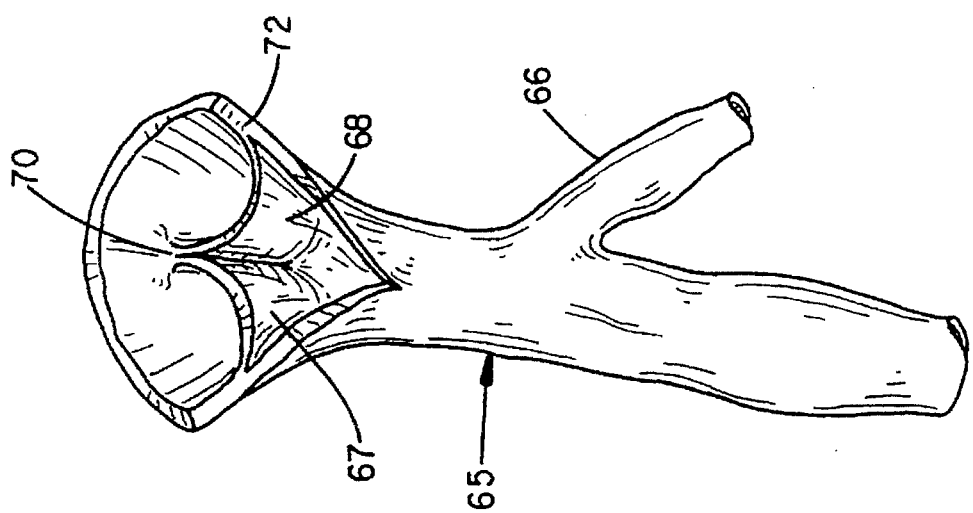
FIG. 9 is a partially sectioned anatomical view of a segment of vein showing a venous valve.

FIGS. 9 and 10 comprise anatomical drawings of a portion of a vein 65. It shows a branch 66 as well as opposed pockets 67 and 68 which meet at 70 to form a tissue cusp therebetween. The valve is shown in its closed state in the view of FIG. 9. With reference to FIG. 10, the upwardly directed arrows represent blood flow toward the heart. This flow opens the valve by compressing the pockets 67 and 68 relative to the wall 72 of the vein. The downwardly directed arrows represent blood flow during diastole, the retrograde flow causing the pockets 67 and 68 to fill, closing the valve. It is the purpose of a valvulotomy to cut or ablate the valve tissue to thereby eliminate the ability thereof to control the blood flow direction.

Figure 11:
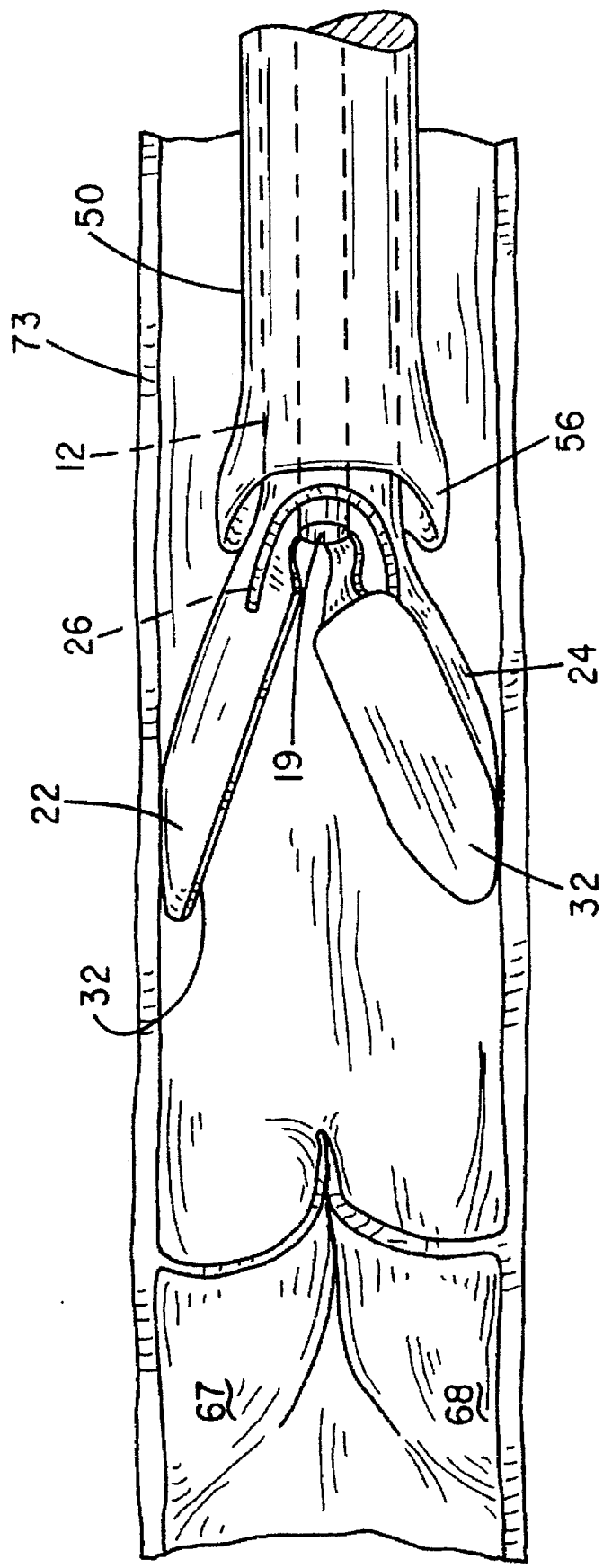
FIG. 11 is a view showing the distal end portion of the instrument of FIG. 1 located in a vein.
Figure 12:
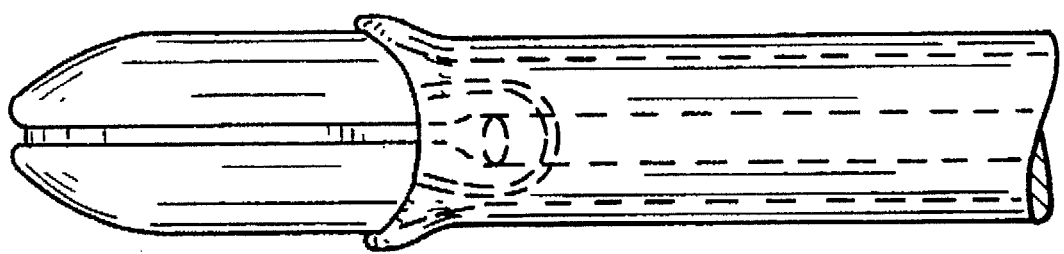
FIG. 12 is a somewhat enlarged partial view of the distal end portion of the instrument of FIG. 1 with the jaws thereof closed.

Referring to FIG. 11, there is shown the distal end portion of the instrument of FIG. 1 deployed within the lumen of a vein 73 and approaching a valve to be disabled. By injecting saline through one of the lumens 18-19 of the inner catheter 12 via port 64 in the handle assembly 42, blood flow in the retrograde direction can be simulated, causing the valve to close, thereby opening the pockets 67 and 68. This allows the hemi-bullet shaped paddles 22 and 24 to enter into them more readily. When the surgeon notes, by tactile response, the engagement of the paddle members 22 and 24 with the tissue comprising the valve, he advances the slide member 52 to advance the outer sheath 50 in the distal direction, closing the jaws against the force of the embedded leaf spring 26, such that the electrodes 32 will be closely spaced, but with the tissue comprising the venous valve cusps therebetween. Now, by activating a RF generator (not shown) by means of a foot switch control or the like, RF energy is delivered, via the electrodes, to cut through the tissue comprising the valve cusp, and effectively precluding it thereafter from controlling the directionality of blood flow through the vein. The instrument may now be advanced further in the distal direction to the site of the next valve in the vein where the process is repeated.

In that it is desirable that at least a portion of the valve cusp be removed rather than simply bisected, the use of the electrode configuration represented by the drawings of FIGS. 5 and 8 may be preferred. Even though the valve cusp tissue is thin, the lesser amount remaining within the wall of the vein tends to lead to a lesser disruption in laminar flow of blood later when the segment of vein is used as a bypass graft.

By employing a relatively blunt, smoothly curved, instrument rather than the sharp blades or hooks of the prior art, and by using RF ablation of the valve cusps, there is a resulting reduction in the remaining valve tissue and attendant reduction in damage to the delicate lining of the vein wall, especially at the site of vein branches.

As already mentioned, the central lumen of the catheter 12 can also accommodate an optical-fiber bundle, allowing the surgeon to see a distance beyond the tips of the paddles, thus facilitating their precise placement in the pockets defining the valve cusps.

The amount of valve cusp material ablated is determined by the construction of the electrodes, which can be in the shape of a flat broad surface as shown in FIGS. 3 and 6, a thin line as shown in FIGS. 4 and 7 or in a loop as shown in FIGS. 5 and 8. The valve is therefore destroyed in accordance with the shape and design of the electrodes from a simple bifurcation to a complete removal of a predetermined portion of the valve proximate the cusps thereof. Because the destruction of the valve cusps is by the RF energy, and not by mechanical cutting using a sharp blade or hook, accidental injury to the endothelium is minimized. The smooth, rounded edges of the paddles further adds to the efficacy of the procedure in that accidental destruction in cutting through the wall of the vein or tearing at the branches is eliminated. In the embodiment of FIG. 1, where the paddles are movable, the relatively wide open space between the paddles facilitates their entering and engaging the valve cusps. Subsequently, the paddles may be closed to press the membranous valve pocket material between them. After the valve material is ablated using RF energy, the paddles are reopened and the catheter is ready to be moved downstream to the next pair of valve pockets to be ablated. The process continues until all of the valves in the bypass vein graft segment have been severed.

Since the paddles 22 and 24 are inwardly movable by controlled actuation of the slide 52 on the handle member 42, the same catheter can accommodate a significant gradient in vein sizes. As the saphenous vein, for example, becomes smaller in going distally from the thigh toward the ankle, moving the paddles closer together will allow the catheter to be passed down to narrower segments without having to exchange instruments or to create another surgical opening through the vein wall as with prior art, rigid, mechanical cutting valvulotomes. This again translates into improved safety and simplicity.

Another important advantage of the RF valvulotome of the present invention is that the destruction of the valve tissue is independent of mechanical cutting strokes that have heretofore been necessary when attempting to cut through the relatively strong membranous tissue. Moreover, the flexible polymeric tubular nature of the instrument of the present invention is in contrast to the rather rigid traditional metallic valvulotomes. Maneuvering down a tortuous vein, thus, becomes easier and trauma to the vein wall will also be reduced.

Figure 13:
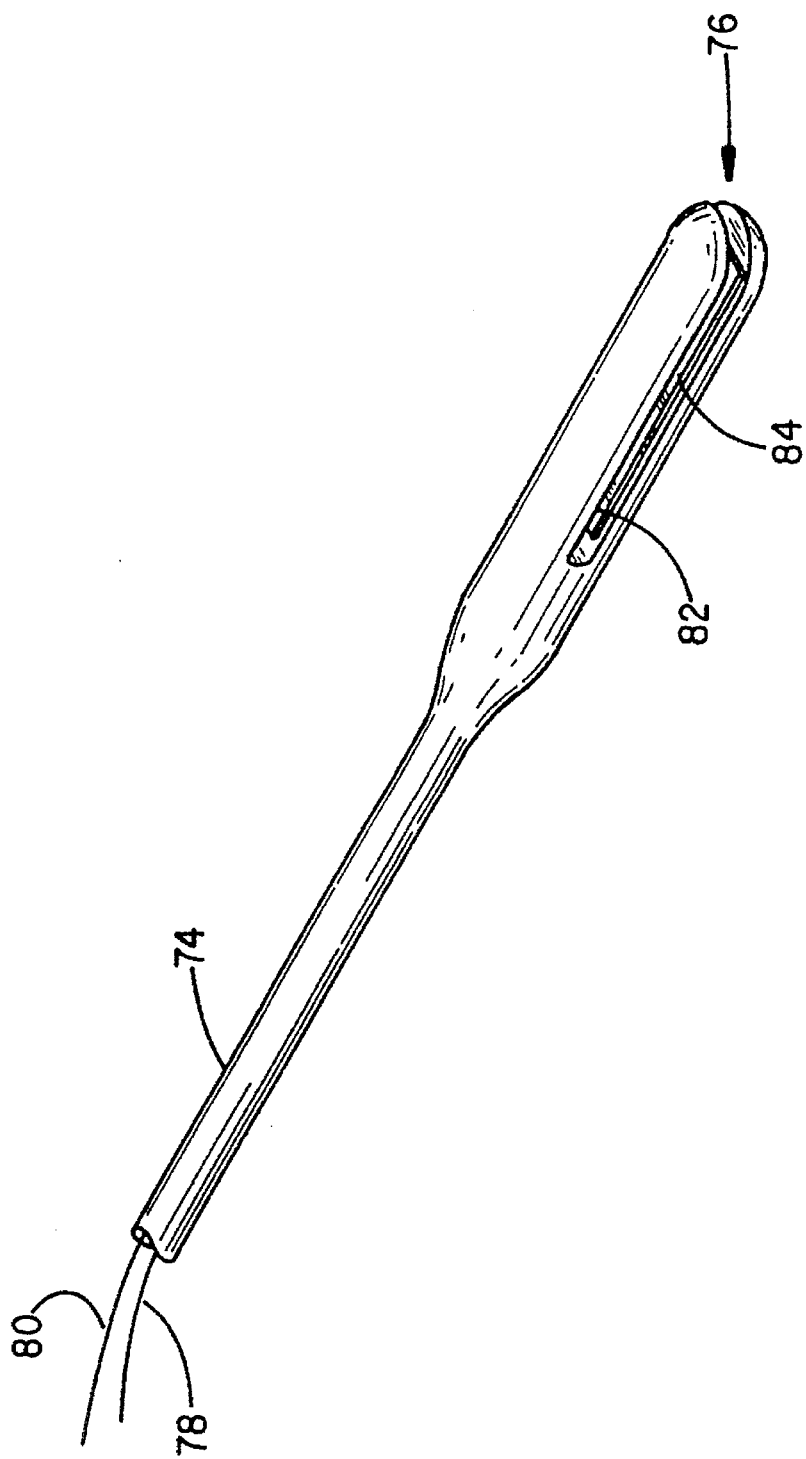
FIG. 13 is a drawing showing an alternative design for an electrosurgical valvulotome.

Referring next to FIG. 13, there is illustrated a further embodiment of the present invention especially designed for use in veins having smaller internal diameters. It comprises an elongated flexible polymeric rod 74 having a slot 76 formed in the rounded distal end thereof. Wires 78 and 80 are embedded within the polymeric material so as to be insulated from one another and they electrically connect at their distal ends to the metallization patterns 82 and 84 formed on the surfaces defining the slot 76. By eliminating the internal lumen for accommodating viewing optics or a saline flush, the overall diameter of the polymeric rod 74 may be reduced, allowing use in small diameter veins. The rounded distal end is significantly more atraumatic than prior art valvulotomes.

In this arrangement, the rod 74 is advanced such that the portions of the pocket defining the valve cusp fit between the electrode members 82 and 84. Again, RF energy is applied from a suitable electrosurgical generator of conventional design causing a concentrated current flow between the electrodes 82 and 84 and through the tissue contained between them. This energy is sufficient to effect ablation of the valve cusps.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A bipolar electrosurgical instrument for performing a valvulotomy procedure on a vein to disable venous valves contained therein comprising:

(a) an elongated, flexible catheter having a proximal end, a distal end and at least one lumen extending therebetween, the catheter being of a cross-sectional size permitting its insertion into a vein to be treated and having at the distal end thereof first and second spaced-apart paddle members dimensioned to fit within opposing pockets defining cusps of venous valves, the paddle members having opposed facing surfaces, each with a pattern of metallization thereon, and (b) a pair of conductors insulated from one another extending through the at least one lumen from the proximal end and individually electrically joined to the pattern of metallization on the spaced-apart paddle members.

2. The bipolar electrosurgical instrument as in claim 1 wherein the opposed facing surfaces are flat.

3. The bipolar electrosurgical instrument as in claim 1 at least one of the opposed facing surfaces is convex.

4. The bipolar electrosurgical instrument as in one of claims 1 through 3 wherein the pattern of metallization on the opposed facing surface of the first paddle member is of a greater area than the pattern of metallization on the opposed facing surface of the second paddle member.

5. The bipolar electrosurgical instrument as in one of claims 1 through 3 wherein the pattern of metallization on the opposed facing surface of one of the first and second paddle members comprises a loop.

6. The bipolar electrosurgical instrument as in claim 4 wherein the pattern of metalization on the opposed facing surface of the second paddle member is rectilinear.

7. The bipolar electrosurgical instrument as in claim 1 wherein said first and second spaced apart paddle members are movable relative to each other, allowing the spacing between the opposed facing surfaces to be varied.

8. The bipolar electrosurgical instrument as in either of claims 1 or 7 wherein the paddle members are hemi-bullet shaped.

9. The bipolar electrosurgical instrument as in claim 8 wherein the pattern of metallization on the opposed facing surface of the first paddle member is of a greater area than the pattern of metallization on the opposed facing surface of the second paddle member.

10. The bipolar electrosurgical instrument as in claim 8 wherein the pattern of metallization on the opposed facing surface of one of the first and second paddle members comprises a loop.

11. The bipolar electrosurgical instrument as in claim 8 wherein the pattern of metallization on the opposed facing surface of the second paddle member is rectilinear.

12. The bipolar electrosurgical instrument as in claim 1 and further including:

(a) a second lumen extending the length of the catheter; and (b) means at the proximal end of the catheter for injecting a liquid through the second lumen for closing a valve in the vein being treated distal of the distal end of the catheter thereby facilitating inserting of the paddle members into the opposing pockets defining the cusps of the venous valves.

13. The bipolar electrosurgical instrument as in claim 1 and further including:

(a) a second lumen extending the length of the catheter; and (b) an optical fiber bundle contained within the second lumen, said optical fiber bundle including at least one illumination fiber and a plurality of viewing fibers; and (c) means at the proximal end of the catheter adapted to connect a light source to the at least one illumination fiber and the plurality of viewing fibers to a visual display device.

14. A bipolar electrosurgical instrument for performing a valvulotomy procedure on a vein to disable venous valves contained therein, comprising:

(a) an elongated, flexible catheter having a proximal end, a distal end and at least one lumen extending therebetween, the catheter being of a cross-sectional size permitting its insertion into a vein to be treated and having at its distal end thereof first and second relatively movable jaw members dimensioned to fit within opposing pockets defining cusps of the venous valves, the jaw members having opposed facing surfaces, each with a pattern of metallization thereon;

(b) a pair of conductors insulated from one another extending through the at least one lumen from the proximal end and individually electrically joined to the pattern of metallization on the spaced-apart jaw members; and (c) means disposed at the proximal end of the catheter and operatively coupled to the jaw members for controlling the spacing between the opposed facing surfaces of the jaw members.

15. The bipolar electrosurgical instrument as in claim 14 wherein the means for controlling comprises:

(a) a tubular sheath coaxially surrounding the catheter and longitudinally movable relative thereto, the sheath having a distal end portion for engaging the first and second jaw members; and (b) handle means operatively connected to the proximal end of the catheter and to the tubular sheath for imparting longitudinal displacement to the tubular sheath relative to the catheter.

16. The bipolar electrosurgical instrument as in claim 14 and further including means for normally biasing the first and second jaw members away from one another.

17. The bipolar electrosurgical instrument as in claim 14 wherein the opposed facing surfaces are flat.

18. The bipolar electrosurgical instrument as in claim 14 at least one of the opposed facing surfaces is convex.

19. The bipolar electrosurgical instrument as in any one of claims 14 through 18 wherein the pattern of metallization on the opposed facing surface of the first jaw member is of a greater area than the pattern of metallization on the opposed facing surface of the second jaw member.

20. The bipolar electrosurgical instrument as in one of claims 14 through 18 wherein the pattern of metallization on the opposed facing surface of the first jaw member comprises a loop.

21. The bipolar electrosurgical instrument as in claim 19 wherein the pattern of metalization on the opposed facing surface of the second jaw member is rectilinear.

22. The bipolar electrosurgical instrument as in claim 14 wherein the first and second jaw members are each hemi-bullet shaped.

23. The bipolar electrosurgical instrument as in claim 14 and further including:
  (a) a second lumen extending the length of the catheter; and
  (b) means at the proximal end of the catheter for injecting a liquid through the second lumen for closing a valve in the vein being treated distal of the distal end of the catheter thereby facilitating inserting of the jaw members into the opposing pockets defining the cusps of the venous valves.

24. The bipolar electrosurgical instrument as in claim 14 and further including:

(a) a second lumen extending the length of the catheter; and
  (b) an optical fiber bundle contained within the second lumen, said optical fiber bundle including at least one illumination fiber and a plurality of viewing fibers; and
  (c) means at the proximal end of the catheter adapted for connecting a light source to the at least one illumination fiber and the plurality of viewing fibers to a visual display device.

25. A method for performing a valvulotomy procedure comprising the steps of:
  (a) forming an incision through the wall of a vein at a predetermined location therealong;
  (b) inserting a catheter having a pair of paddle members at a distal end thereof through the incision, the paddle members of the pair each having opposed facing surfaces separated by a gap, the facing surfaces including electrodes comprising a pattern of metallization on the facing surfaces;
  (c) advancing the catheter through the vein until the cusps of a valve to be disabled are positioned in the gap;
  (d) applying RF energy between the electrodes sufficient to ablate the cusps; and
  (e) repeating steps (c) and (d) for each valve encountered as the catheter is advanced in an upstream direction relative to normal direction of blood flow in the vein.

* * * * *